(12) United States Patent
Takahashi et al.

(10) Patent No.: US 8,569,232 B2
(45) Date of Patent: Oct. 29, 2013

(54) THERAPEUTIC AGENT FOR DIABETES

(75) Inventors: Yutaka Takahashi, Hyogo (JP); Kazuo Chihara, Hyogo (JP)

(73) Assignees: Kobe University, Hyogo (JP); JCR Pharmaceuticals Co., Ltd., Hyogo (JP)

( * ) Notice: Subject to any disclaimer, the term of this patent is extended or adjusted under 35 U.S.C. 154(b) by 562 days.

(21) Appl. No.: 12/740,362

(22) PCT Filed: Oct. 17, 2008

(86) PCT No.: PCT/JP2008/068831
§ 371 (c)(1),
(2), (4) Date: Sep. 21, 2010

(87) PCT Pub. No.: WO2009/057461
PCT Pub. Date: May 7, 2009

(65) Prior Publication Data
US 2011/0046055 A1 Feb. 24, 2011

(30) Foreign Application Priority Data
Oct. 31, 2007 (JP) ................. 2007-284268

(51) Int. Cl.
*A61P 3/10* (2006.01)
*A61K 38/16* (2006.01)
*C07K 14/00* (2006.01)

(52) U.S. Cl.
USPC ................. 514/6.9; 514/7.3; 530/350

(58) Field of Classification Search
None
See application file for complete search history.

(56) References Cited

U.S. PATENT DOCUMENTS

2003/0096299 A1* 5/2003 Wittamer et al. ............. 435/7.1
2004/0086966 A1* 5/2004 Wittamer et al. ............ 435/69.1
2007/0286863 A1* 12/2007 Sinal et al. ................. 424/143.1

FOREIGN PATENT DOCUMENTS

JP 2006-141233 A 6/2006
WO WO 2006/017171 A2 2/2006

OTHER PUBLICATIONS

Matejtschuk, Paul. "Lyophilization of Proteins." Cryopreservation and Freeze-Drying Protocols. vol. 368. pp. 59-72. Jun. 2007.*

International Search Report of PCT/JP2008/068831 (Nov. 12, 2008).
M. Takahashi et al., "Chemerin Enhances Insulin Signaling and Potentiates Insulin-Stimulated Glucose Uptake in 3T3-L1 Adipocytes," FEBS Letters, vol. 582 (2008) pp. 573-578.
K. Bozaoglu et al., "Chemerin is a Novel Adipokine Associated With Obesity and Metabolic Syndrome," Endocrinology, vol. 148, No. 10 (2007) pp. 4687-4694.
K. Goralski et al., "Chemerin, a Novel Adipokine That Regulates Adipogenesis and Adipocyte Metabolism," The Journal of Biological Chemistry, vol. 282, No. 38 (Sep. 21, 2007) pp. 28175-28188.
V. Wittamer et al., "The C-Terminal Nonapeptide of Mature Chemerin Activates the Chemerin Receptor with Low Nanomolar Potency," The Journal of Biological Chemistry, vol. 279, No. 11 (Mar. 12, 2004) pp. 9956-9962.
B. Zabel et al., "Chemokine-Like Receptor 1 Expression and Chemerin-Directed Chemotaxis Distinguish Plasmacytoid from Myeloid Dendritic Cells in Human Blood," The Journal of Immunology, vol. 174 (2005) pp. 244-251.
B. Zabel et al., "Chemerin Activation by Serine Proteases of the Coagulation, Fibrinolytic, and Inflammatory Cascades," The Journal of Biological Chemistry, vol. 280, No. 41 (Oct. 14, 2005) pp. 34661-34666.
V. Wittamer et al., "Specific Recruitment of Antigen-Presenting Cells by Chemerin, a Novel Processed Ligand from Human Inflammatory Fluids," The Journal of Experimental Medicine, vol. 198, No. 7 (Oct. 6, 2003) pp. 977-985.
S. Nagpal et al. "Tazarotene-Induced Gene 2 (TIG2), a Novel Retinoid-Responsive Gene in Skin," J. Invest Dermatol, vol. 109 (1997) pp. 91-95.
D. Rossi et al., "The Biology of Chemokines and Their Receptors," Annu. Rev. Immunol., vol. 18 (2000) pp. 217-242.
I. Charo et al., "Chemokines in the Pathogenesis of Vascular Disease," Circ Res., vol. 95 (2004) pp. 858-866.
E. Kershaw et al., "Adipose Tissue as an Endocrine Organ," The Journal of Clinical Endocrinology & Metabolism, vol. 89, No. 6 (2004) pp. 2548-2556.
G. Fantuzzi et al., "Adipose Tissue, Adipokines, and Inflammation," J. Allergy Clin Immunol., vol. 115 (2005) pp. 911-919.
P. Zimmet et al., "Global and Societal Implications of the Diabetes Epidemic," Nature, vol. 414 (Dec. 13, 2001) pp. 782-787.

* cited by examiner

*Primary Examiner* — Julie Ha
*Assistant Examiner* — Li Ni Komatsu
(74) *Attorney, Agent, or Firm* — Millen, White, Zelano & Branigan, P.C.

(57) ABSTRACT

Disclosed are method for treating diabetes, a protein for treatment of diabetes, and pharmaceutical composition comprising the same. The protein is human mature chemerin, which can be used to treat diabetes, in particular type 2 diabetes, inter alia to treat diabetes in a patient who is concurrently administered with insulin.

8 Claims, 7 Drawing Sheets

A.

B.

SEQUENCE LISTING

```
<160> NUMBER OF SEQ ID NOS: 16

<210> SEQ ID NO 1
<211> LENGTH: 429
<212> TYPE: DNA
<213> ORGANISM: Homo sapiens
<220> FEATURE:
<221> NAME/KEY: CDS
<222> LOCATION: (1)..(429)
<223> OTHER INFORMATION:

<400> SEQUENCE: 1 gag ctc acg gaa gcc cag cgc cgg ggc ctg cag gtg gcc ctg gag gaa      48
Glu Leu Thr Glu Ala Gln Arg Arg Gly Leu Gln Val Ala Leu Glu Glu
1               5                   10                  15 ttt cac aag cac ccg ccc gtg cag tgg gcc ttc cag gag acc agt gtg      96
Phe His Lys His Pro Pro Val Gln Trp Ala Phe Gln Glu Thr Ser Val
                20                  25                  30 gag agc gcc gtg gac acg ccc ttc cca gct gga ata ttt gtg agg ctg     144
Glu Ser Ala Val Asp Thr Pro Phe Pro Ala Gly Ile Phe Val Arg Leu
            35                  40                  45 gaa ttt aag ctg cag cag aca agc tgc cgg aag agg gac tgg aag aaa     192
Glu Phe Lys Leu Gln Gln Thr Ser Cys Arg Lys Arg Asp Trp Lys Lys
        50                  55                  60 ccc gag tgc aaa gtc agg ccc aat ggg agg aaa cgg aaa tgc ctg gcc     240
Pro Glu Cys Lys Val Arg Pro Asn Gly Arg Lys Arg Lys Cys Leu Ala
65                  70                  75                  80 tgc atc aaa ctg ggc tct gag gac aaa gtt ctg ggc cgg ttg gtc cac     288
Cys Ile Lys Leu Gly Ser Glu Asp Lys Val Leu Gly Arg Leu Val His
                85                  90                  95 tgc ccc ata gag acc caa gtt ctg cgg gag gct gag gag cac cag gag     336
Cys Pro Ile Glu Thr Gln Val Leu Arg Glu Ala Glu Glu His Gln Glu
```

```
                    100                 105                 110
acc cag tgc ctc agg gtg cag cgg gct ggt gag gac ccc cac agc ttc      384
Thr Gln Cys Leu Arg Val Gln Arg Ala Gly Glu Asp Pro His Ser Phe
        115                 120                 125 tac ttc cct gga cag ttc gcc ttc tcc aag gcc ctg ccc cgc agc          429
Tyr Phe Pro Gly Gln Phe Ala Phe Ser Lys Ala Leu Pro Arg Ser
    130                 135                 140

<210> SEQ ID NO 2
<211> LENGTH: 143
<212> TYPE: PRT
<213> ORGANISM: Homo sapiens

<400> SEQUENCE: 2

Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
                20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
        50                  55                  60

Pro Glu Cys Lys Val Arg Pro Asn Gly Arg Lys Arg Lys Cys Leu Ala
65                  70                  75                  80

Cys Ile Lys Leu Gly Ser Glu Asp Lys Val Leu Gly Arg Leu Val His
                85                  90                  95

Cys Pro Ile Glu Thr Gln Val Leu Arg Glu Ala Glu Glu His Gln Glu
            100                 105                 110

Thr Gln Cys Leu Arg Val Gln Arg Ala Gly Glu Asp Pro His Ser Phe
        115                 120                 125

Tyr Phe Pro Gly Gln Phe Ala Phe Ser Lys Ala Leu Pro Arg Ser
    130                 135                 140

<210> SEQ ID NO 3
<211> LENGTH: 6
<212> TYPE: PRT
<213> ORGANISM: Homo sapiens

<400> SEQUENCE: 3

Lys Ala Leu Pro Arg Ser
1               5

<210> SEQ ID NO 4
<211> LENGTH: 411
<212> TYPE: DNA
<213> ORGANISM: Homo sapiens
<220> FEATURE:
<221> NAME/KEY: CDS
<222> LOCATION: (1)..(411)
<223> OTHER INFORMATION:

<400> SEQUENCE: 4 gag ctc acg gaa gcc cag cgc cgg ggc ctg cag gtg gcc ctg gag gaa      48
Glu Leu Thr Glu Ala Gln Arg Arg Gly Leu Gln Val Ala Leu Glu Glu
1               5                   10                  15 ttt cac aag cac ccg ccc gtg cag tgg gcc ttc cag gag acc agt gtg      96
Phe His Lys His Pro Pro Val Gln Trp Ala Phe Gln Glu Thr Ser Val
                20                  25                  30 gag agc gcc gtg gac acg ccc ttc cca gct gga ata ttt gtg agg ctg      144
Glu Ser Ala Val Asp Thr Pro Phe Pro Ala Gly Ile Phe Val Arg Leu
            35                  40                  45
```

```
gaa ttt aag ctg cag cag aca agc tgc cgg aag agg gac tgg aag aaa      192
Glu Phe Lys Leu Gln Gln Thr Ser Cys Arg Lys Arg Asp Trp Lys Lys
 50                  55                  60 ccc gag tgc aaa gtc agg ccc aat ggg agg aaa cgg aaa tgc ctg gcc      240
Pro Glu Cys Lys Val Arg Pro Asn Gly Arg Lys Arg Lys Cys Leu Ala
 65                  70                  75                  80 tgc atc aaa ctg ggc tct gag gac aaa gtt ctg ggc cgg ttg gtc cac      288
Cys Ile Lys Leu Gly Ser Glu Asp Lys Val Leu Gly Arg Leu Val His
                 85                  90                  95 tgc ccc ata gag acc caa gtt ctg cgg gag gct gag gag cac cag gag      336
Cys Pro Ile Glu Thr Gln Val Leu Arg Glu Ala Glu Glu His Gln Glu
            100                 105                 110 acc cag tgc ctc agg gtg cag cgg gct ggt gag gac ccc cac agc ttc      384
Thr Gln Cys Leu Arg Val Gln Arg Ala Gly Glu Asp Pro His Ser Phe
        115                 120                 125 tac ttc cct gga cag ttc gcc ttc tcc                                  411
Tyr Phe Pro Gly Gln Phe Ala Phe Ser
130                 135
```

<210> SEQ ID NO 5
<211> LENGTH: 137
<212> TYPE: PRT
<213> ORGANISM: Homo sapiens

<400> SEQUENCE: 5

```
Glu Leu Thr Glu Ala Gln Arg Arg Gly Leu Gln Val Ala Leu Glu Glu
1               5                  10                  15

Phe His Lys His Pro Pro Val Gln Trp Ala Phe Gln Glu Thr Ser Val
                20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
 50                  55                  60

Pro Glu Cys Lys Val Arg Pro Asn Gly Arg Lys Arg Lys Cys Leu Ala
 65                  70                  75                  80

Cys Ile Lys Leu Gly Ser Glu Asp Lys Val Leu Gly Arg Leu Val His
                 85                  90                  95

Cys Pro Ile Glu Thr Gln Val Leu Arg Glu Ala Glu Glu His Gln Glu
            100                 105                 110

Thr Gln Cys Leu Arg Val Gln Arg Ala Gly Glu Asp Pro His Ser Phe
        115                 120                 125

Tyr Phe Pro Gly Gln Phe Ala Phe Ser
130                 135
```

<210> SEQ ID NO 6
<211> LENGTH: 24
<212> TYPE: DNA
<213> ORGANISM: Artificial
<220> FEATURE:
<223> OTHER INFORMATION: Primer f1

<400> SEQUENCE: 6
ggatcctgag ctcacggaag ccca                                           24

<210> SEQ ID NO 7
<211> LENGTH: 27
<212> TYPE: DNA
<213> ORGANISM: Artificial
<220> FEATURE:
<223> OTHER INFORMATION: Primer r1

<400> SEQUENCE: 7

```
ctcgagttag ctgcggggca gggcctt                                          27

<210> SEQ ID NO 8
<211> LENGTH: 23
<212> TYPE: DNA
<213> ORGANISM: Artificial
<220> FEATURE:
<223> OTHER INFORMATION: Primer f2

<400> SEQUENCE: 8
catatggagc tcacggaagc cca                                              23

<210> SEQ ID NO 9
<211> LENGTH: 27
<212> TYPE: DNA
<213> ORGANISM: Artificial
<220> FEATURE:
<223> OTHER INFORMATION: Primer r2

<400> SEQUENCE: 9
ggatccttag ctgcggggca gggcctt                                          27

<210> SEQ ID NO 10
<211> LENGTH: 37
<212> TYPE: DNA
<213> ORGANISM: Artificial
<220> FEATURE:
<223> OTHER INFORMATION: Primer f3

<400> SEQUENCE: 10
cgcggatccc gagcccaaat cttgtgacaa aactcac                               37

<210> SEQ ID NO 11
<211> LENGTH: 46
<212> TYPE: DNA
<213> ORGANISM: Artificial
<220> FEATURE:
<223> OTHER INFORMATION: Primer r3

<400> SEQUENCE: 11
aaggaaaaaa gcggccgctc atttacccgg agacagggag aggctc                     46

<210> SEQ ID NO 12
<211> LENGTH: 76
<212> TYPE: DNA
<213> ORGANISM: Apis mellifera

<400> SEQUENCE: 12
gaattctata aatatgaaat tcttagtcaa cgttgccctt gttttatgg tcgtgtacat        60 ttcttacatc tatgcg                                                      76

<210> SEQ ID NO 13
<211> LENGTH: 76
<212> TYPE: DNA
<213> ORGANISM: Apis mellifera

<400> SEQUENCE: 13
ggatccgcat agatgtaaga aatgtacacg accataaaaa caagggcaac gttgactaag       60
aatttcatat ttatag                                                      76

<210> SEQ ID NO 14
<211> LENGTH: 19
<212> TYPE: DNA
<213> ORGANISM: Artificial
```

```
<220> FEATURE:
<223> OTHER INFORMATION: Primer f4

<400> SEQUENCE: 14
ggatcctgag ctcacggaa                                          19

<210> SEQ ID NO 15
<211> LENGTH: 21
<212> TYPE: DNA
<213> ORGANISM: Artificial
<220> FEATURE:
<223> OTHER INFORMATION: Primer r4

<400> SEQUENCE: 15
ctcgagttag gagaaggcga a                                       21

<210> SEQ ID NO 16
<211> LENGTH: 9
<212> TYPE: PRT
<213> ORGANISM: Apis mellifera

<400> SEQUENCE: 16

Asp Pro Glu Leu Thr Glu Ala Gln Arg
1               5
```

THERAPEUTIC AGENT FOR DIABETES

TECHNICAL FIELD

The present invention relates to treatment of diabetes mellitus in humans, in particular to a method for treatment of diabetes mellitus based on enhancing the action of insulin, and a protein for treatment of diabetes mellitus, and a pharmaceutical composition comprising the protein for treatment of diabetes mellitus.

BACKGROUND ART

Obesity and obesity-related diseases are becoming major health problems in many countries. In advanced counties, especially in those in Western Europe, morbidity and mortality due to obesity have been escalating (Non-patent document 1). In recent years, these events have often been discussed in association with the so-called metabolic syndrome, a condition which occurs by accumulation of visceral fat as one of its causal factors.

In such a circumstance, extensive studies are being made on the mechanisms of development of obesity-related diseases, and it is getting clear that incretion compounds which are secreted from adipocytes (adipokines) engage closely in their development. For example, it has been clarified that leptin, adiponectine and resistin, among adipokines, regulate the energy homeostasis of the cells and their sensitivity to insulin (Non-patent documents 2 and 3). Further, adipocytes secrete inflammatory cytokines, which have long been known to be secreted from macrophages, such as TNF-α, and proteins like MCP-1, which plays a role in obtaining resistance to insulin (lowering sensitivity of the cells to insulin) (Non-patent documents 4 and 5). These compounds also may be regarded as a kind of adipokines. In addition to these, many other adipokines have been observed to be expressed in the course of differentiation of preadipocytes into adipocytes.

As mentioned above, clarifying the functions of adipokines secreted from adipocytes is very important for elucidation of the etiology of obesity-related diseases including diabetes and the so-called metabolic syndrome, and further for the development of effective, new ways of treating them.

Among obesity-related diseases, the number of patients with diabetes exceeds 7 million in Japan alone, and the number is increasing rapidly. In other developed countries also, the situation is largely the same as that in Japan. Diabetes is a systemic disorder of metabolism caused by abnormal increase in blood sugar levels due to a lowered ability of regulating blood sugar levels (glucose tolerance), and is characterized in that it extremely deteriorates the quality of life (QOL) not only by causing severe metabolic disorders like hyperosmolar coma and ketoacidosis, but also by leading to bad prognosis due to microangiopathic complications. Diabetes is generally classified into type 1 diabetes, which is caused by destruction of pancreatic β-cells (autoimmune disorders are considered to be the primary cause), and type 2 diabetes, which is a combination of insulin resistance and reduction in insulin secretion.

In type 2 diabetes, which accounts for about 90% of diabetic patients, the insulin action is weakened through a combination at varying proportions of lowered insulin secretion from pancreatic β-cells and insulin resistance in those cells which insulin targets, such as those in skeletal muscles, resulting in hyperglycemia. Besides, persistent insulin resistance leads to a vicious circle of β-cells being exhausted to further weaken in its ability of secreting insulin, thus the symptoms exacerbate. For type 2 diabetes, it is expected that such agents that can reduce insulin resistance would work very effectively, for they could terminate the vicious cycle.

As therapeutics for type 2 diabetes, mitiglinide calcium hydrate tablets (trade name: Glufast tablets), and pioglitazone hydrochloride tablets (trade name: Actos tablets) are already on the market. However, it is not yet possible to address all the patient with type 2 diabetes whose etiology is not fully understood and which has a variety of backgrounds. Thus, development of novel agents have been hoped for which have a different mechanism of action from those of conventional ones.

Chemerin (also called TIG2 or metabokine) is a chemotactic factor for macrophages and non-differentiated dendritic cells, and is a ligand for the G protein-coupled receptor (ChemR23) (Non-patent documents 6 and 7). It is reported that chemerin, as a chemotactic factor for a specific population of immunomodulatory antigen presenting cells, has a function to regulate immune responses at sites of inflammation and injury (Non-patent documents 8 and 9).

Human chemerin is translated as a protein consisting of 163 amino acids, and after secreted as a precursor produced by processing at its signal peptide consisting of 20 amino acid at its N-terminus (human prochemerin) (its nucleotide sequence shown as SEQ ID NO:1 and amino acid sequence as SEQ ID NO:2, respectively), 6 amino acids at its C-terminus (amino acid sequence: Lys-Ala-Leu-Pro-Arg-Ser: SEQ ID NO:3) is removed to form human mature chemerin (its nucleotide sequence shown in SEQ ID NO:4 and amino acid sequence in SEQ ID NO:5) consisting of 137 amino acids and having high affinity for ChemR23 (Non-patent documents 7 and 10).

Recently, it has been reported that chemerin is a member of adipokines, which take part in differentiation of adipocytes (Non-patent document 11), and that the blood concentration of chemerin corresponds with body mass index (BMI), triglycerides concentration in blood, and blood pressure (Non-patent document 12). However, the role of chemerin in regulation of metabolism has not been elucidated.

[Non-patent document 1] Nature, 414:782-7 (2001)
[Non-patent document 2] J Allergy Clin Immunol, 115: 911-9 (2005); quiz 920
[Non-patent document 3] Endocrinol Metab, 89: 2548-56 (2004)
[Non-patent document 4] Circ Res, 95: 858-66 (2004)
[Non-patent document 5] Annu Rev Immunol, 18: 217-42 (2000)
[Non-patent document 6] J Invest Dermatol, 109: 91-5 (1997)
[Non-patent document 7] J Exp Med, 198: 977-85 (2003)
[Non-patent document 8] J Biol Chem, 280: 34661-6 (2005)
[Non-patent document 9] J Immunol, 174: 244-51 (2005)
[Non-patent document 10] J Biol Chem, 279: 9956-62 (2004)
[Non-patent document 11] J Biol Chem, 282: 28175-88 (2007)
[Non-patent document 12] Endocrinology, 148: 4687-94 (2007)

DISCLOSURE OF INVENTION

The Problem to be Solved by the Invention

Against the above background, the objective of the present invention is to provide a method for treatment of diabetes, in particular type 2 diabetes, a protein to be used for treatment of diabetes, and a pharmaceutical composition for treatment of diabetes comprising the protein.

Utilizing mouse 3T3-L1 cells, which are preadipocytes, as a model of adipocytes, the present inventors cloned, by the differential display technique, the gene whose expression is induced during the process of differentiation of the cells into adipocytes, detected the gene, and found that the gene is the chemerin gene. Further, the present inventors found that human mature chemerin augments the insulin's activity to promote glucose uptake by 3T3-L1 cells. In addition, the present inventors also found that human mature chemerin augments the hypoglycemic activity of insulin in normal mice as well as in type 2 diabetic model mice. The present invention was completed on the basis of these discoveries.

Thus the present invention provide what follows.

1. A pharmaceutical composition for treatment of diabetes comprising human mature chemerin as an active ingredient.

2. The pharmaceutical composition for treatment of diabetes according to 1 above, wherein the diabetes is type 1 diabetes or type 2 diabetes.

3. The pharmaceutical composition for treatment of diabetes according to 1 above, wherein the diabetes is type 2 diabetes.

4. The pharmaceutical composition for treatment of diabetes according to one of 1 to 3 above, wherein the composition is a hypoglycemic pharmaceutical composition.

5. The pharmaceutical composition for treatment of diabetes according to one of 1 to 4 above, wherein the composition is an insulin activity-augmenting pharmaceutical composition.

6. The pharmaceutical composition for treatment of diabetes according to one of 1 to 5 above, wherein the composition is a pharmaceutical composition for treatment of diabetes for a patient who is concurrently administered with insulin.

7. The pharmaceutical composition for treatment of diabetes according to one of 1 to 6 above, wherein the composition is in the form of an injection.

8. The pharmaceutical composition for treatment of diabetes according to 7 above, wherein the injection is an aqueous preparation comprising human mature chemerin.

9. The pharmaceutical composition for treatment of diabetes according to 7 above, wherein the injection is a lyophilizate comprising human mature chemerin.

10. The pharmaceutical composition for treatment of diabetes according to one of 1 to 9 above, wherein the human mature chemerin comprises the amino acid sequence shown as SEQ ID NO:5.

11. A method for treatment of diabetes in a patient comprising administering to the patient a therapeutically effective amount of human mature chemerin.

12. The method according to 11 above, wherein the diabetes is type 1 diabetes or type 2 diabetes.

13. Human mature chemerin for treatment of diabetes.

14. The human mature chemerin according to 13 above, wherein the diabetes is type 1 diabetes or type 2 diabetes.

The Effect of the Invention

Human mature chemerin augments the activity of insulin to stimulating glucose uptake by cells, thereby augmenting the hypoglycemic activity of insulin. Therefore, human mature chemerin can be used for treatment of diabetes. And a pharmaceutical composition comprising it according to the present invention can, through augmentation of the activity of the intrinsic insulin of a patient, or of insulin administered to the patient, promote uptake of blood sugar by cells, and thereby effectively lower the blood sugar levels compared with insulin administered alone. Thus, while the pharmaceutical composition according to the present invention can be used both for type 1 diabetes as well as type 2 diabetes, it is particularly suitable for type 2 diabetes, which is accompanied by insulin resistance, for it augments the activity of insulin to promote glucose uptake by cells. Further, as the pharmaceutical composition according to the present invention augments the activity of insulin, the pharmaceutical composition according to the present invention, administered alone, can lower the blood sugar levels without concurrent administration of insulin, in a patient in whom enough amount of intrinsic insulin is secreted, and in the case where the amount of intrinsic insulin secreted in a patient is low or substantially lacking, the pharmaceutical composition may be used together with supplementary insulin which is concurrent administered.

Furthermore, because the pharmaceutical composition for treatment of diabetes according to the present invention comprises a ligand for G protein-coupled receptor (ChemR23) and is thought to act via ChemR23, thus having entirely different mechanism of action from those of conventional agents, the pharmaceutical composition can be used as a therapeutic agent for treatment of those diabetic patients who are resistant to conventional agents.

BEST MODE FOR CARRYING OUT THE INVENTION

Figure 1:
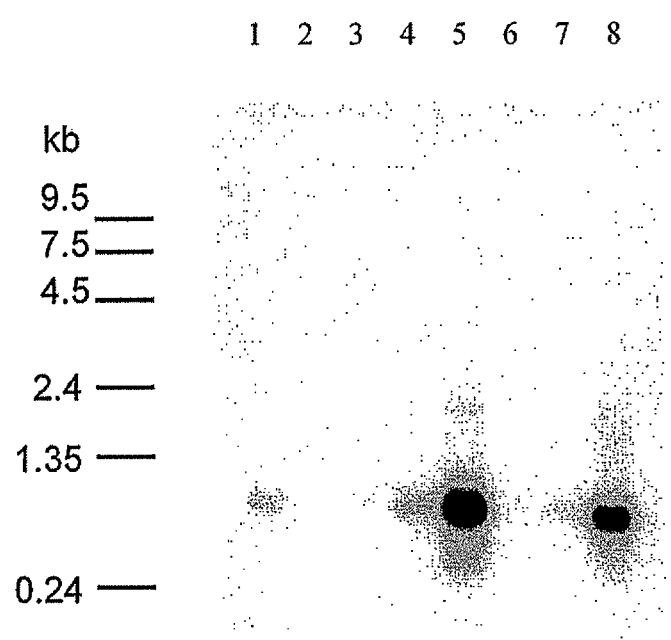
FIG. 1 shows Northern blotting of mRNAs extracted from various human organs, using human chemerin cDNA as a probe. The origins of mRNAs: Lane 1: heart, lane 2: brain, lane 3: placenta, lane 4: lung, lane 5: liver, lane 6: skeletal muscle, lane 7: kidney, and lane 8: pancreas.

In the present invention, a "patient" treated with human mature chemerin is a mammalian animal including a human, and is preferably a human.

The pharmaceutical composition for treatment of diabetes according to the present invention comprises human mature chemerin as an active ingredient. In the present invention, "human mature chemerin" includes not only the wild-type human mature chemerin (i.e., a protein formed by removal of the signal peptide portion and 6 amino acid at the C-terminus from the human chemerin immediately after its production by translation in a human: SEQ ID NO:5) but also proteins which have one or two amino acid residues (e.g., Asp-Pro, or the like) added at the N-terminus of the wild-type protein, insofar as they act to augment the activity of insulin. Such addition of one or two amino acids at the N-terminus does not have any substantial influence on the activity of wild-type human mature chemerin. In particular, though, due to technical restraints, such one or two additional residues at the N-terminus may sometimes be left behind after the process of formation of an exogenous protein in host cells using genetic recombination technique, human mature chemerin containing such additional amino acid residues can generally be used in exactly the same manner as in the natural human mature chemerin containing no such additional amino acid residues.

In the present invention, human mature chemerin may be produced as a recombinant protein using the genetic recombination technique. In such a case, E. coli, mammalian cells such as CHO cells, or insect cells can be used as a host which constitutes an expression system.

The pharmaceutical composition for treatment of diabetes comprising human mature chemerin as an active ingredient according to present invention may be administered in the form of an injection, intravenously, intramuscularly, intraperitoneally, or subcutaneously. Among these, subcutaneous administration is more preferred. The pharmaceutical composition for treatment of diabetes according to the present invention may be supplied in the form of a lyophilized preparation or an aqueous preparation. An aqueous preparation may be provided in the form of filled vials, or supplied in the form of prefilled-type preparations in which it is already filled in syringes. A lyophilized preparation is used after dissolved in an aqueous medium.

The pharmaceutical composition for treatment of diabetes according to the present invention comprising human mature chemerin as an active ingredient may be used concurrently with an insulin preparation. In such a case, the pharmaceutical composition for treatment of diabetes comprising human mature chemerin may be administered before, at the same time, or after the administration of an insulin preparation. In those cases, the pharmaceutical composition for treatment of diabetes according to the present invention may also be supplied in the form of a kit for treatment of diabetes in combination with an insulin preparation. A kit may take such a form in which an insulin preparation (an ampule, vial or prefilled-type preparation) and a human mature chemerin preparation according to the present invention (an ampule, vial or prefilled-type preparation) are contained in combination in a single container. In this case, the insulin preparation may be the same as or similar to a conventional one that have been generally used. In addition, when insulin and human mature chemerin are to be administered at the same time, the pharmaceutical composition for treatment of diabetes according to the present invention may be in the form of a single preparation containing the human mature chemerin and insulin, both in an therapeutically effective amount.

Though in the present invention, the dose of human mature chemerin is a matter to be determined by a physician in charge based on the degree of insulin resistance and the degree of reduced secretion of insulin in the patient, in the case where the secretion of patient's intrinsic insulin is low and the patient is to be administered with both insulin and human mature chemerin, human mature chemerin can be administered at a proportion of 50-1000 mg per 100 unit of insulin, for example. If patient's intrinsic insulin is secreted in a substantial amount and thus human mature chemerin is administered alone without insulin administration, the dose of human mature chemerin may be 10-200 mg/adult/day, for example.

Further, the pharmaceutical composition for treatment of diabetes according to the present invention may be administered concurrently with mitiglinide calcium hydrate, pioglitazone hydrochloride or other agents for treatment of diabetes, within a range in which they are acceptable causing no severe side effects.

The pharmaceutical composition for treatment of diabetes according to the present invention may be in the form of an injection which is prepared by mixing chemerin with a sterile aqueous medium or a nonaqueous medium. As a sterile aqueous medium, water for injection may be employed, and as a sterile nonaqueous medium, one may choose and use as desired one of those media known by those skilled in the art as media for nonaqueous injections, such as propylene glycol, polyethylene glycol, sesame oil, soybean oil, corn oil, propylene glycol fatty acid esters, and the like. A particularly preferred medium is an aqueous medium, and inter alia, water. Further, the pharmaceutical composition for treatment of diabetes according to the present invention may as desired contain various additives which are commonly employed in injectable preparations. Major examples of such additives include isotonic agents, buffers, preservatives, stabilizers, pH adjusting agents and the like.

In the above, examples of isotonic agents include salts such as sodium chloride and the like. Examples of buffers include phosphate buffer, citrate buffer, acetate buffer, malonate buffer, succinate buffer and the like. Examples of preservatives include chlorobutanol, benzyl alcohol, p-hydroxybenzoate esters (methylparaben, propylparaben), sorbic acid, phenethyl alcohol, phenol, dehydroacetic acid and the like. Examples of stabilizers include albumin, globulin, sorbitol, ethylene glycol, propylene glycol, sodium sulfite and the like. Examples of pH adjusting agents include inorganic acids such as hydrochloric acid, sulfuric acid, phosphoric acid and the like; organic acids such as acetic acid, tartaric acid, lactic acid, citric acid, succinic acid, malonic acid, oxalic acid, benzoic acid, gluconic acid, fumaric acid, sorbic acid and the like; inorganic bases such as sodium hydroxide, sodium bicarbonate, sodium carbonate, and the like; organic bases such as sodium citrate, sodium tartrate, sodium succinate, sodium malonate, sodium gluconate and the like. Though there is no particular limitation as to the pH, it may be around neutral pH, e.g., at or near pH 7.4, for example.

EXAMPLES

While the present invention will be described in further detail below with reference to examples, it is not intended that the present invention be limited to the examples. Besides, all the animal experiments were conducted in accordance with the guidelines of Ethics Committee, School of Medicine, Kobe University.

<Differentiation of 3T3-L1 Cells into Adipocytes>

3T3-L1 cells, mouse preadipocytes, are most commonly used cells in studying differentiation of preadipocytes into adipocytes in vitro (Cell 5:19-27 (1975)). 3T3-L1 cells (purchased from American Type Culture Collection (ATCC)) were subcultured in Dulbecco's modified Eagle's medium (DMEM medium) containing 10% FCS. Induction of differentiation of 3T3-L1 cells into adipocytes was conducted in the manner as already reported, i.e., following the procedure as mentioned below (Life Sci, 68: 2917-23 (2001)). Namely, after the cells were cultured for 48 hours in DMEM medium containing 250 nmol/L dexamethasone, 0.5 nmol/L 1-methyl-3-isobutyl-xanthine, and 10 µg/mL insulin supplemented with 10% FCS, the medium was exchanged with DMEM medium containing 10 µg/mL insulin and supplemented with 10% FCS, and culture was continued for further 48 hours.

<Differential Display Technique>

From 3T3-L1 cells (5×10$^7$ cells in each case), before and after differentiation, respective mRNAs were extracted using QuickPrep mRNA Purification Kit (GE Healthcare Biosciences). Using ReverTra Ace™ (Toyobo), cDNA solution was prepared from 0.5 µg mRNAs. Namely, to 0.5 µL of the cDNA solution was added 4.5 µL of a PCR solution containing 2 µM dNTPs, 5 µCi [$^{33}$P]dATP (3000 Ci/mmol, New England Nuclear), AmpliTaq (Perkin-Elmer), 1 µM anchor primer (T12MN, Clontech) and 0.5 µM arbitrary primer (10 mer, GC ratio=40-60%, Clontech). PCR performed consisted of one cycle of [94° C.: 3 min, 40° C.: 3 min, 72° C.: 5 min] and 35 cycles of [94° C.: 30 sec, 40° C.: 2 min, 72° C.: 30 sec], and the final reaction at 72° C. for 5 minutes. The DNA fragments labeled with $^{33}$P by PCR were subjected to 6% polyacrylamide gel electrophoresis, and an X-ray film was overlaid on the gel for exposure. The X-ray film then was developed. The electrophoretic patterns of the DNA fragments obtained by the PCR from the cDNAs of each of the cells, before and after differentiation, were compared on these X-ray films. The bands whose density was found to have changed on the X-ray films after differentiation as compared with before differentiation were regarded as corresponding to fragments of the genes whose expression was induced along with the differentiation of adipocytes. The gel was cut-out at the positions corresponding to those bands, and PCR was performed in the same condition as the above using the gel as a template. The PCR product thus obtained was subcloned into pGEM-T Easy Vector (Promega).

DNA sequencing was performed by a conventional manner on the 318 clones obtained by the subcloning, and revealed that a clone was included which contained a fraction of the gene for mouse chemerin.

<Cloning of Human Prochemerin Gene>

A homology search was performed on the nucleotide sequence of mouse chemerin gene obtained by the differential display technique using GENEBANK, which gave the DNA sequence encoding human prochemerin (SEQ ID NO:1). Using human adipose tissue cDNA (Clontech) as a template, PCR was performed with primer f1 (5'-GGATCCTGAGCT-CACGGAAGCCCA-3': SEQ ID NO:6) and primer r1 (5'-CTCGAGTTAGCTGCGGGGCAGGGCCTT-3': SEQ ID NO:7) using ReverTra Ace™ (Toyobo) to amplify the cDNA encoding human prochemerin. PCR performed consisted of 35 cycles of [94° C.: 1 min, 55° C. 1 min, 72° C.: 2 min], and the final reaction at 72° C. for 5 min. Human prochemerin cDNA thus amplified was inserted into pCR2.1 vector (Novagen). The plasmid thus obtained was designated pCR2.1-chemerin.

<Northern Blotting> pCR2.1-chemerin was digested with NdeI and XhoI to cut out human prochemerin cDNA. The cut-out cDNA was radiolabeled with [$^{32}$P]dCTP (10 mCi/mL, Amersham Biosciences) to give a probe using Rediprime II Random Prime Labeling System (Amersham Biosciences). Northern blotting was performed by letting the above radiolabeled probe hybridize, in a conventional manner, with Human 8-lane Multiple Tissue Northern Blot (BD Bioscience), which consisted of RNAs originating from heart, brain, placenta, lung, liver, skeletal muscle, kidney and spleen transferred onto a nylon membrane for Northern blotting. As a result, expression of human chemerin was detected mainly in the liver and pancreas (FIG. 1).

<Preparation of Polyclonal Antibody>

Figure 2:
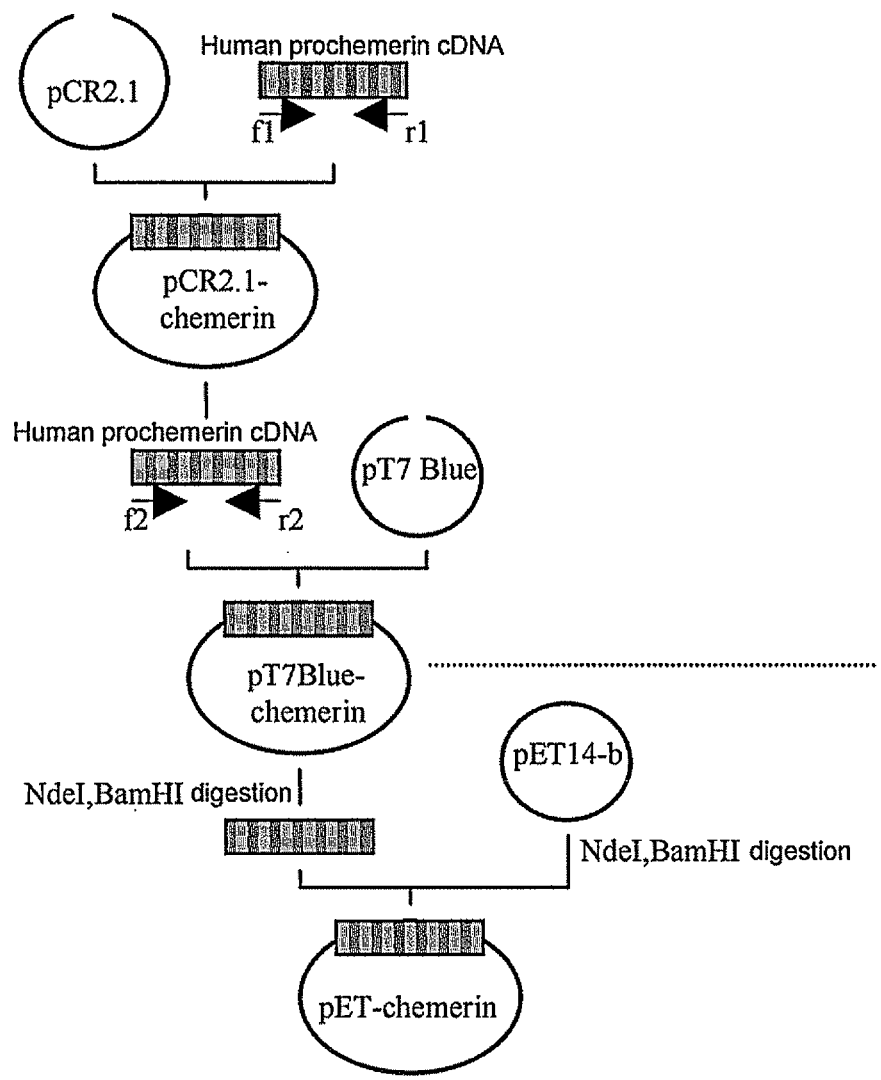
FIG. 2 is a process diagram illustrating the method of constructing vectors for expression of human prochemerin and human mature chemerin.
Figure 3:
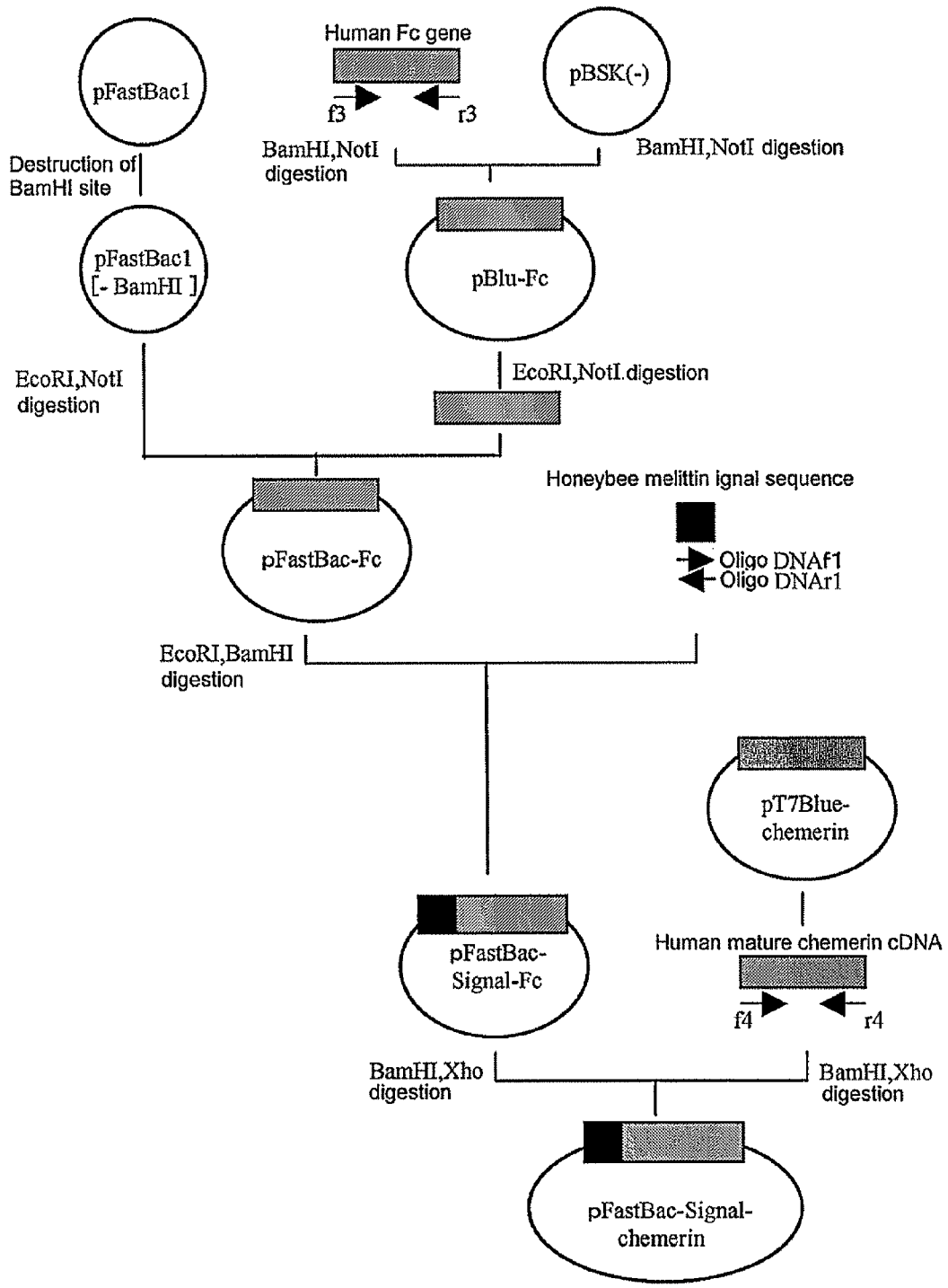
FIG. 3 is a process diagram illustrating the method of constructing vectors for expression of human prochemerin and human mature chemerin.

Human prochemerin cDNA was amplified using pCR2.1-chemerin as a template, primer f2 (5'CATATGGAGCT-CACGGAAGCCCA-3': SEQ ID NO:8) and primer r2 (5'-GGATCCTTAGCTGCGGGGCAGGGCCTT-3': SEQ ID NO:9). PCR reaction performed consisted of 35 cycles of [94° C.: 1 min, 55° C.: 1 min, 72° C.: 2 min] and the final reaction at 72° C. for 5 minutes. Human prochemerin cDNA thus amplified was inserted into pT7BlueT vector (Novagen). This plasmid thus formed was named pT7Blue-chemerin. Human prochemerin was cut out by digesting pT7Blue-chemerin with NdeI and BamHI, and inserted into pET14-b vector (Novagen) which had been digested with NdeI and BamHI. This plasmid thus formed was named pET-chemerin. The method for construction of pET-chemerin is shown schematically in FIG. 2 and FIG. 3. The human prochemerin obtained using pET-chemerin, which has histidine added at the N-terminus, was named His-tag human prochemerin.

E. coli ADA494(DE3) was transformed with pET-chemerin. The transformed E. coli cells were suspended in 2 L of LB medium and cultured at 37° C., and when OD600 reached about 0.4, IPTG was added to the medium at the concentration of 0.4 mM, and culture was continued for further 3 hours. After the culture, the E. coli cells were collected by centrifugation, washed once with 20 mM sodium phosphate buffer (pH 7.5) containing 500 mM sodium chloride and 0.1% Triton X-100, and after suspended in a cell disintegrator solution [20 mM sodium phosphate buffer (pH 7.5) containing 500 mM sodium chloride and 0.1% Triton X-100], the cells were subjected to ultrasonic disintegration. Cell debris was removed by centrifugation and the supernatant thus obtained was filtered through a 0.22 µm filter, and was passed through a HiTrap chelating HP column (Amersham Biosciences) which had been equilibrated with the cell disintegrator solution. The column was washed with 5 volumes of the cell disintegrator solution, and His-tag human prochemerin was eluted with the cell disintegrator solution supplemented with 200 mM imidazole. The eluate collected then was passed through a Superdex 200 column (Amersham Biosciences) which had been equilibrated with 20 mM sodium phosphate buffer containing 1 mM 2-mercaptoethanol, 1 mM DTT, 500 mM sodium chloride and 0.1% Triton X-100, and His-tag human prochemerin was collected. A rabbit was sensitized by a conventional method using His-tag human prochemerin thus collected, and antiserum containing anti-human His-tag human prochemerin antibody was obtained.

<Construction of a Baculovirus Vector for Expression of Human Mature Chemerin> pFastBac-1 (GIBCO-BRL) was digested with BamHI, and after the sticky end formed by BamHI was blunt ended with Klenow fragment (Toyobo), subjected to self-ligation using Ligation kit Ver. 2 (TAKARA) to destroy the BamHI site of pFastBac-1. This plasmid was named pFastBac1[-BamHI].

Using a human spleen cDNA library (Takara Bio) as a template, and primer f3 (5'-CGCGGATCCCGAGOC-CAAATCTTGTGACAAAACTCAC-3': SEQ ID NO:10) and primer r3 (5'AAGGAAAAAAGCGGCCGCTCATT-TACCCGGAGACAGGGAGAGGCTC-3': SEQ ID NO:11), Fc gene of human IgG was amplified by PCR. PCR performed consisted of 35 cycles of [94° C.: 3 min, 55° C.: 1 min, 72° C.: 2 min] and the final reaction at 72° C. for 5 minutes. The PCR product was digested with BamHI and NotI, and incorporated into pBluescriptSK(-)(pBSK(-), STRATAGENE) which had been digested with BamHI and NotI. This plasmid was named pBlu-Fc.

pBlu-Fc was digested with EcoRI and NotI to cut out Fc gene fragment, which then was incorporated into pFastBac1-[-BamHI] which had been digested with EcoRI and NotI. This plasmid was named pFastBac-Fc.

The 5'-end of two complementary oligoDNAs which encode honeybee melittin signal sequence, oligoDNA f1 (5'-GAATTCTATAAATATGAAATTCTTAGT-CAACGTTGCCCTTGTTTTTATGGTCGTG-TACATTTCTTACATCTATGCG-3': SEQ ID NO:12) and oligoDNA r1 (5'-GGATCCGCATAGATGTAAGAAATG-TACACGACCATAAAAACAAGGGCAACGT-TGACTAAGAATTTCATATTTATAG-3': SEQ ID NO:13) was phosphorylated with T4 polynucleotide kinase (TOYOBO), and they was annealed to form a double-stranded DNA, which then was incorporated into pFastBac-Fc which had been digested with EcoRI and BamHI. This was named pFastBac-Signal-Fc.

Using pT7Blue-chemerin as a template and primer f4 (5'-GGATCCTGAGCTCACGGAA-3': SEQ ID NO:14) and primer r4 (5'CTCGAGT-TAGGAGAAGGCGAA-3': SEQ ID NO:15), human mature chemerin cDNA was amplified. Human mature chemerin cDNA thus amplified was digested with BamHI and XhoI, and subjected to a ligation reaction with pFastBac-Signal-Fc which had been digested with BamHI and XhoI. Five µL of this ligation reaction mixture was mixed with 50 µL of DH10Bac Competent *E. coli* cells (Invitrogen) for Bacmid construction and let stand on ice for 30 minutes. After heat shock was applied to this, 0.5 mL of SOC medium which had been warmed at 37° C. was added and mixed, and culture was continued for 5 hours at 37° C. The culture was diluted 2000-fold with LB medium, and 0.2 mL of this dilution was spread on LB plates (50 µg/mL kanamycin, 7 µg/mL gentamicin, 10 µg/mL tetracycline, IPTG/Xgal coated). This was cultured for 2 days at 37° C. After the culture, a large white colony of *E. coli* on the plate was selected, and from this clone was purified Bacmid DNA, which was used as baculovirus vector for human mature chemerin expression (pFastBac-Signal-chemerin). Using pFastBac-Signal-chemerin, human mature chemerin can be expressed in insect cells as a secretory protein, with a melittin signal sequence added at the N-terminus, and following expression, the melittin signal being removed, human mature chemerin is secreted in the medium. A method for generation of pFastBac-Signal-chemerin is shown schematically in FIG. 3.

<Generation of Recombinant Baculovirus for Human Mature Chemerin Expression>

Sf9 cells suspended in Grace's Insect Cell Culture Medium (Invitrogen) containing 10% FCS were spread onto 6-well plates at $1.5 \times 10^6$ cells/2 mL per well, and the plates were let stand for 1.5 hours at 27° C. to allow the cells to adhere to the plates. The medium was removed from the plates, and the cells were washed with 2 mL/well of Grace's Insect Cell Culture Medium, supplement-free, (Invitrogen), and following addition of 2 mL/well of Grace's Insect Cell Culture Medium, supplement-free, let stand for 10 minutes at 27° C. Five µL of Cellfectin (Invitrogen) was mixed with 100 µL of Grace's Insect Cell Culture Medium, supplement-free, and with this mixture was further admixed with a blend of 5-µL solution of baculovirus vector for human mature chemerin expression and 100 µL of Grace's Insect Cell Culture Medium, supplement-free, and the mixture was let stand for 30 minutes at 27° C. To this then was added 800 µL of Grace's Insect Cell Culture Medium, supplement-free, to form Bacmid-Cellfection mixture solution. The medium was removed from the plates, and following addition of 1 mL/well of Bacmid-Cellfection mixture solution, the plates were let stand for 5 hours at 27° C. This then was washed with 2 mL/well of Grace's Insect Cell Culture Medium containing 10% FCS, and following addition of 2 mL/well of the same medium, culture was conducted for 3 days at 27° C. After the culture, the culture supernatant was collected and centrifuged (3000 rpm, 5 min) to remove remaining cell debris to obtain a seed virus solution for human mature chemerin expression (seed virus solution for expression). The seed virus solution for expression was stored at 4° C. until use.

<Large Scale Preparation of Baculovirus for Human Mature Chemerin Expression>

Sf9 cells were suspended at a density of $0.8 \times 10^6$ cells/mL in Grace's Insect Cell Culture Medium containing 10% FCS, and 10 mL of this suspension was placed in a 75-cm$^2$ culture flask. By letting stand for one hour at 27° C., the cells were allowed to adhere to the flask. The medium was removed, and a solution then was added which was a blend of 4 mL of the above medium and 1 mL of the seed virus solution for expression, and the viral infection was allowed to take place by one hour of slow shake at room temperature. The supernatant was removed, and 10 mL/flask of the above medium was added, and culture was continued for 3 days at 27° C. After the culture, the culture supernatant was collected and centrifuged (3000 rpm, 5 min) to remove cell debris to obtain a viral solution for human mature chemerin expression. The viral solution for human mature chemerin expression was stored at 4° C. until use.

<Expression of Recombinant Human Mature Chemerin>

High-Five™ cells were suspended at the density of $2.5 \times 10^6$ cells/mL in Grace's Insect Cell Culture Medium containing 10% FCS, and 20 mL of this suspension was placed in a 150 cm$^2$-culture flask (15 in number). The cells were let stand for one hour at 27° C. to allow them to adhere to the flask. After the culture supernatant was removed, a blend of 9.5 mL of the above medium and 0.5 mL of the viral solution for chemerin expression was added, and viral infection was allowed to take place by one hour of gentle shaking at room temperature. The supernatant was removed, 20 mL/flask of Ex-Cell 405 medium (JRH Biosciences) was added, and culture was continued for 3 days at 27° C. The culture supernatant was collected and centrifuged (3000 rpm, 5 min) to remove cell debris, and the supernatant was collected, which was filtered through a 0.22 µm filter.

<Purification of Human Mature Chemerin>

The supernatant collected above was dialyzed against 100 mM HEPES buffer (pH 7.0). This then was passed through SP Sepharose (HiTrap SP XL, GE Healthcare Bio-Sciences, column size: 5 mL) which had been equilibrated with 50 mM HEPES buffer (pH 7.0) to let human mature chemerin be adsorbed by the resin. After the resin was washed with 5 bed volumes of 50 mM HEPES buffer (pH 7.0), the human mature chemerin which had been adsorbed to the resin was eluted using a concentration gradient of sodium chloride. The main peak, which appeared at the sodium chloride concentration of about 400 mM, was collected. The collected eluate was passed through Tricorn Superdex 75 (100/300) which had been equilibrated with PBS, and the main peak was collected as human chemerin.

Figure 4:
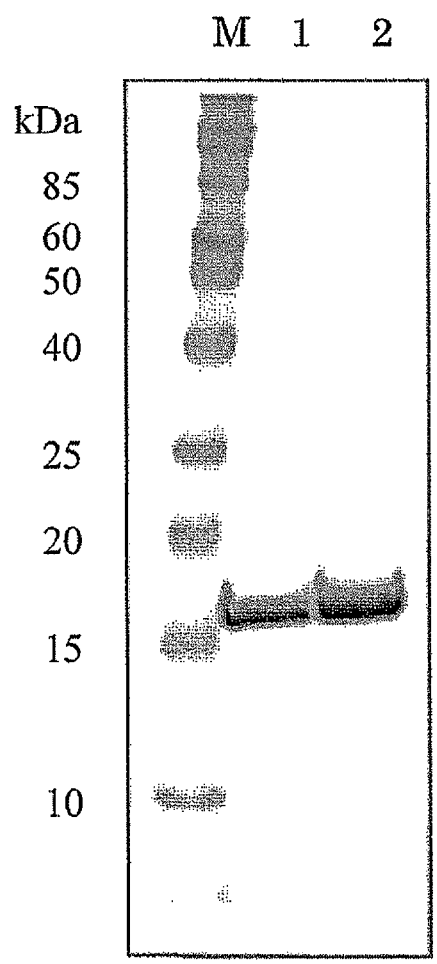
FIG. 4 shows an SDS-PAGE gel electrophoresis pattern of purified human mature chemerin. (A) Coomassie staining. "M" indicates a molecular weight marker. Three μg of the protein was applied to lane 1, and 5 μg to lane 2. (B) Western blotting. "M" indicates a molecular weight marker.
Figure 4:
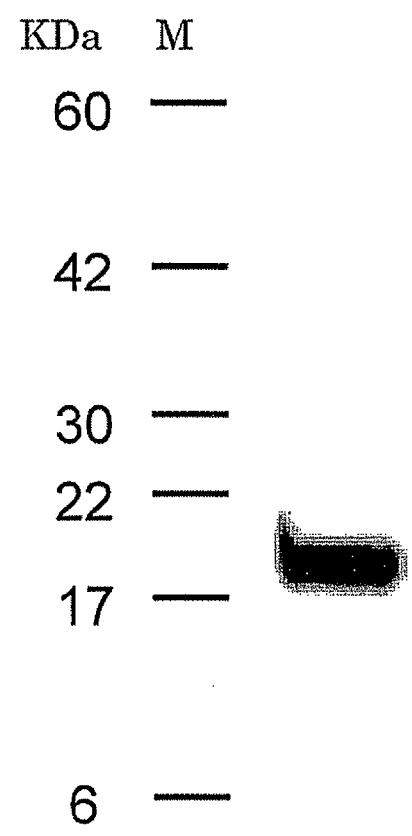

Human mature chemerin was subjected to acrylamide gel electrophoresis using 10-20% gradient gel (PAG mini "Daiichi" 10/20, Daiichi Pure Chemicals Co., Ltd.), and the gel was Coomassie stained. As a result, a band appeared at the position corresponding to the molecular weight calculated from the amino acid sequence of human mature chemerin (FIG. 4A). Also, in Western blotting using anti-His-tag human chemerin antibody, staining was observed at the same position as the band shown in the acrylamide gel electrophoresis, confirming this band as human mature chemerin (FIG. 4B).

<Amino Acid Sequence Analysis at N-Terminus of Human Mature Chemerin>

The collected human mature chemerin was subjected to acrylamide gel electrophoresis using 10-20% gradient gel (PAG mini "Daiichi" 10/20, Daiichi Pure Chemicals Co., Ltd.), and the protein was transferred from the gel onto PVDF membrane using semi-dry blotting. The PVDF membrane was stained with Ponceau 3R, and cut out at the spot of the stained protein and after decolorized in 20% methanol, subjected to analysis for amino acid sequence at its N-terminus on a protein sequencer, Procise492HT (Applied Biosystems). As a result, a sequence made of nine amino acids was read at the N-terminus (Asp-Pro-Glu-Leu-Thr-Glu-Ala-Gln-Arg: SEQ ID NO:16). Two amino acid residues from the N-terminus (i.e., Asp-Pro-) originated from melittin signal sequence, and the amino acid sequence consisting of seven amino acids that followed fully matched with the expected amino acid sequence of human mature chemerin. Thus, the human mature chemerin purified here is a protein consisting of natural human mature chemerin and two amino acids (Asp-Pro-), which originated from melittin signal sequence, added to the N-terminus of the former.

<Influence of Human Mature Chemerin on the Amount of Glucose Uptake by Athpocytes>

Influence of human mature chemerin on the amount of glucose taken up by 3T3-L1 cells was examined by a method previously reported (Biochem J. 1990; 271: 201-207). Namely, 3T3-L1 adipocytes, i.e., 3T3-L1 cells which had differentiated into adipocytes, were cultured for 12 hours in the presence of 100 ng/mL human mature chemerin (chemerin-added group), and after further addition of human insulin at a concentration of $10^{-8}$ M or $10^{-7}$ M, cultured for 15 minutes. A group to which no human mature chemerin was added was named "no-chemerin-added group", which also was subjected to culture for 15 minutes after addition of human insulin at a concentration of $10^{-8}$ M or $10^{-7}$ M. To each culture then was added 0.5 µCi of [1,2-$^3$H]2-deoxy-D-glucose (NEN Life Science Products), and culture was continued for further 15 minutes. After the culture, the cells were washed three times with PBS. The cells then were lysed by addition of 0.2 M NaOH, and the radioactivity was measured on a liquid scintillation counter to determine the amount of glucose taken up by the cells. The amount of glucose was calculated in the amount per unit protein (mg). The experiment was performed three times, and comparison was made between chemerin-added group and no-chemerin-added group according to t-test, and the results was regarded as statistically significant for a p value <0.05.

Figure 5:
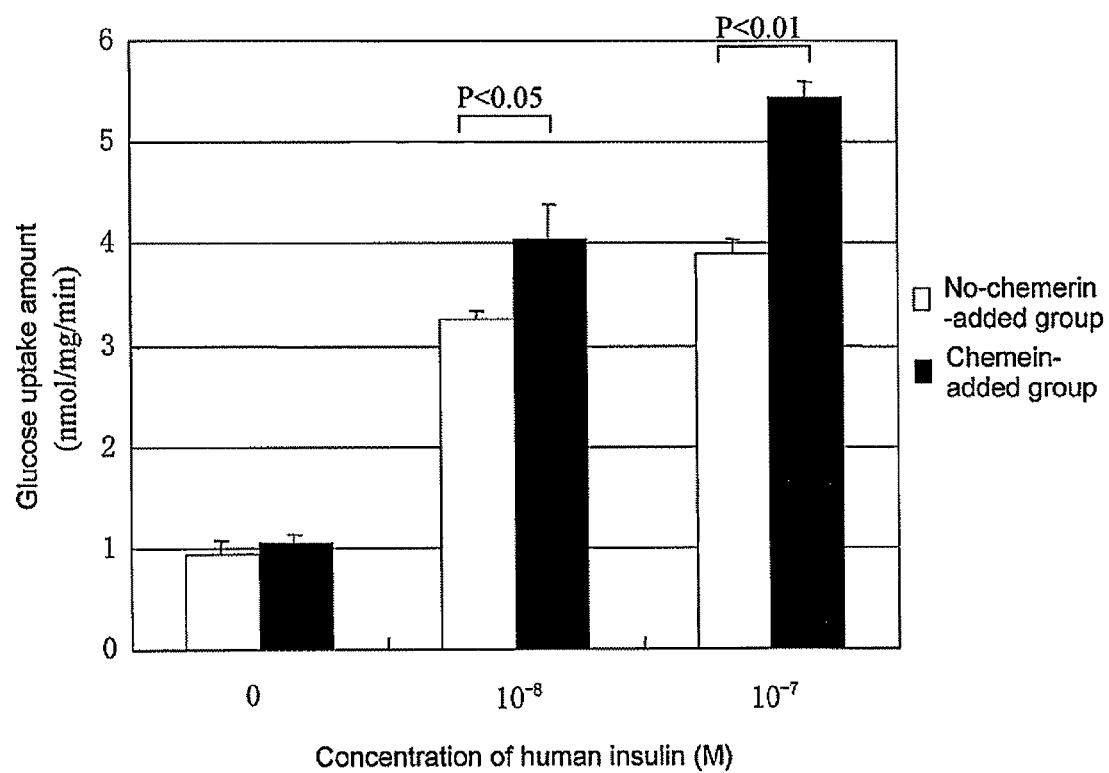
FIG. 5 shows the influence of human mature chemerin on human insulin-induced promotion of glucose uptake by preadipocytes. Vertical bars indicate standard deviations.

As compared with no-chemerin-added group, the amount of glucose taken up was greatly increased in chemerin-added group after addition of human insulin at a concentration of $10^{-8}$ M and $10^{-7}$ M, the difference between the groups was statistically significant. On the other hand, in the case where no human insulin was added, no difference was observed between chemerin-added group and no-chemerin-added group, thus no increase in glucose uptake by adipocytes was shown following addition of human mature chemerin (FIG. 5). These results indicate that human mature chemerin, though it alone does not influence on glucose uptake by adipocytes, acts to augment the human insulin activity to promote glucose uptake by adipocytes.

<Influence of Human Mature Chemerin on Hypoglycemic Effect of Human Insulin on Normal Mice>

Male C57BL/6J mice were kept under the condition of 12-hrs on/off switching of light and at a constant room temperature, allowing free access to feed and water, and those reached 8-week old were used in the experiment. The mice were fasted from the day before the experiment, and 18 hours after the start of fasting, they were peritoneally administered with 40 µg of human mature chemerin dissolved in 200 µL of PBS (chemerin-administered group). Mice to which was administered 200 µL PBS instead of human mature chemerin were designated as the control group. The number of animals of each group was 9. Forty-five minutes after the administration of human mature chemerin, the animals of both groups were administered with 0.009 unit human insulin (Wako Pure Chemical Industries). About 5 µl, of blood was sampled over time from the orbital venous plexus, and blood sugar concentration was measured using a blood sugar measurement device (GlucoCard Alfa GT-1660, ARKRAY, Inc.). Comparison was made using t-test between the chemerin-added group and the control group, and the difference was regarded as statistically significant for a p value <0.05.

Figure 6:
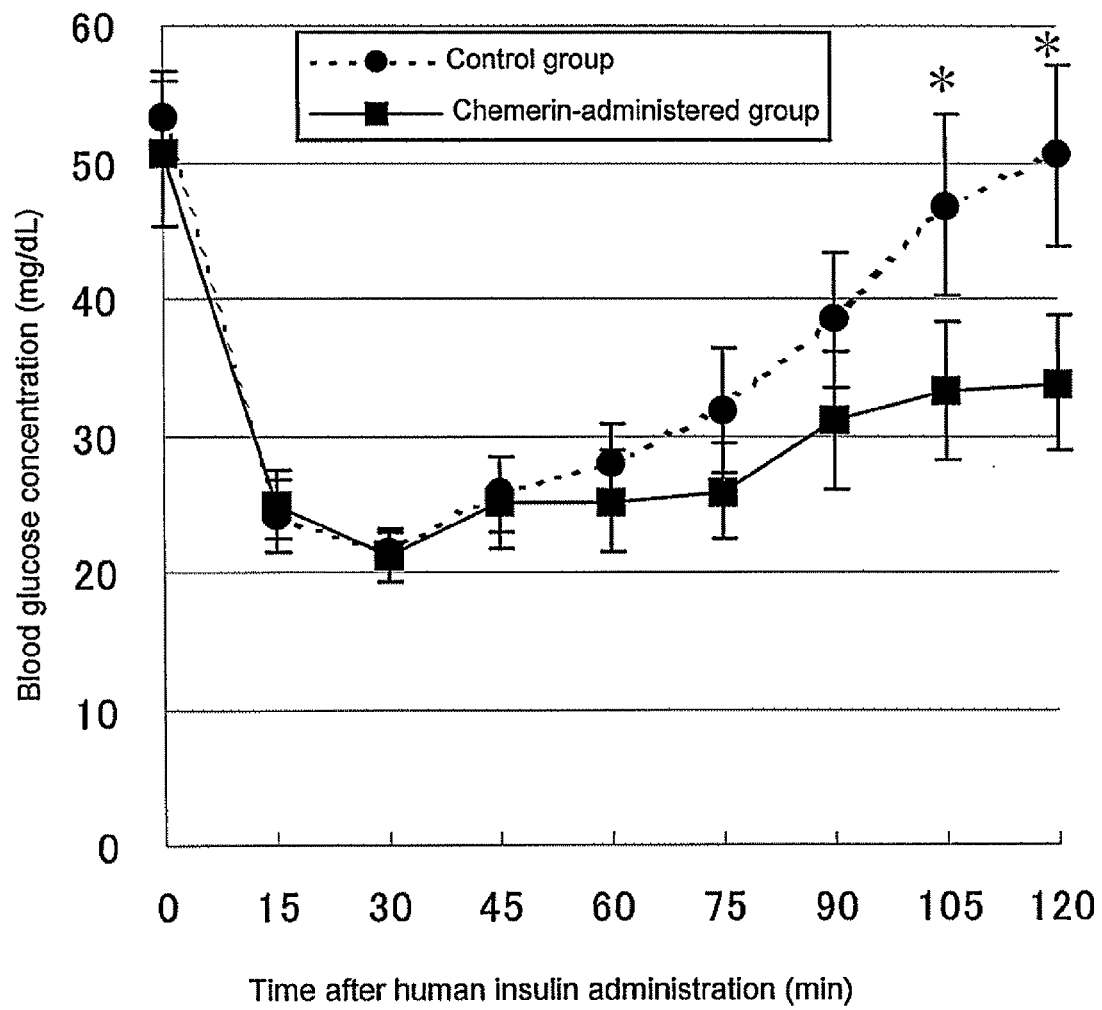
FIG. 6 shows the influence of human mature chemerin on the hypoglycemic activity of human insulin in normal mice. Vertical bars indicate standard deviations, and asterisks $p<0.05$ according to t-test.

While blood sugar levels were 50-55 mg/dL in both groups before administration, it rapidly lowered 15 minutes after administration of human insulin in both groups, showing their minimum values (about 20 mg/dL) 30 minutes after administration. There was no difference in blood sugar levels at this point in time between the groups. This lowering in blood sugar is due to the action of insulin (FIG. 6). Thereafter, blood sugar levels gradually recovered, and returned to those observed before administration in the control group 120 minutes after administration. On the other hand, recovery of blood sugar levels was slow in the chemerin-administered group compared with the control group, namely the chemerin-administered group showed definitely low blood glucose levels compared with the control group 75-120 minutes after administration. In particular, the differences between the groups were statistically significant 105 and 120 minutes after administration. These results indicate that human chemerin has an activity to sustain the hypoglycemic effect of insulin for an extended period of time.

<Influence of Human Mature Chemerin on Hypoglycemic Activity of Human Insulin in Type 2 Diabetic Model Mice>

Human mature chemerin then was examined for its effect of augmenting sensitivity to human insulin using a C57BL+ S/J–m+/+Lepr$^{db}$ mouse (db/db mouse, Clea), a type 2 diabetic model mouse which lacks leptin receptor. Male db/db mice were kept under the condition of 12-hrs on/off switching of light and at a constant room temperature, allowing free access to feed and water, and those reached 7 week old were used in the experiment. The mice were fasted from the day before the experiment, and 20 hours after the start of fasting, they were peritoneally administered with 100 µg of human mature chemerin dissolved in 250 µL of PBS (chemerin-administered group), Mice to which was administered 250 µL of PBS instead of human mature chemerin were designated as the control group. The number of animals of each group was 9. One and half hours after the administration of human mature chemerin, 0.06 unit of human insulin (Wako Pure Chemical Industries) was administered. About 5 µL of blood was sampled over time from the orbital venous plexus, and blood glucose concentration was measured using a blood sugar measurement device (GlucoCard Alfa GT-1660, ARKRAY, Inc.). Comparison was made using t-test between the chemerin-added group and the control group, and the difference was regarded as statistically significant for a p value <0.05.

Figure 7:
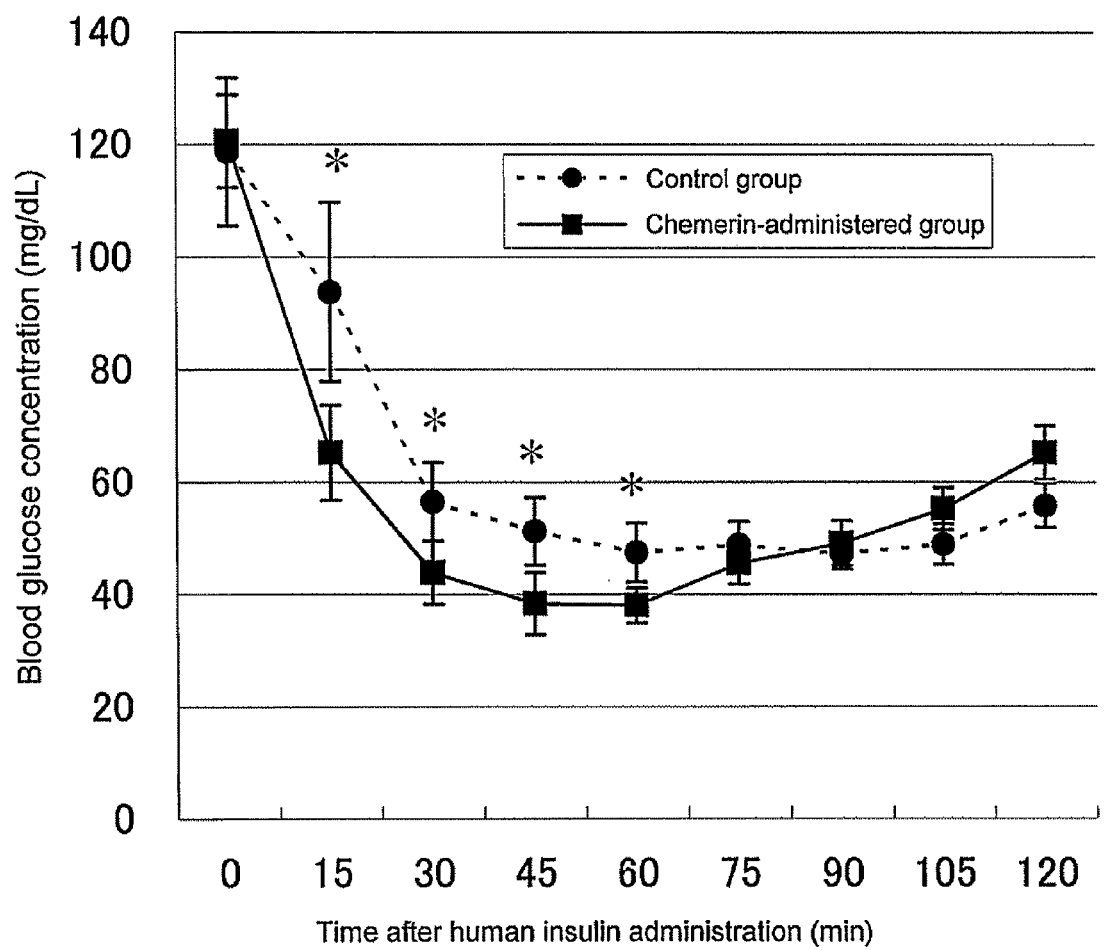
FIG. 7 shows the influence of human mature chemerin on the hypoglycemic activity of human insulin in type 2 diabetic model mice.

The blood sugar levels were about 120 mg/dL in both groups before administration. Though blood sugar levels rapidly lowered 15 minutes after administration of human insulin in both groups, the values in chemerin-administered group was remarkably lower than those in the control group: about 62 mg/dL in chemerin-administered group and about 95 mg/dL in the control group (FIG. 7). The tendency like this continued up to 60 minutes after the administration, and the differences between the groups were statistically significant. The difference between the groups was not observable 75 minutes after the administration and thereafter. These results indicate that human mature chemerin augments the hypoglycemic activity of insulin in type 2 diabetic mice to which it is administered.

| [Preparation Example 1] | Aqueous injection |
|---|---|
| Human mature chemerin | 50 mg |
| Sodium chloride | 9 mg |
| Water for injection | to 1 mL in total volume |

In accordance with the above ratios among the ingredients, human mature chemerin and sodium chloride are dissolved in water for injection to make an aqueous injection.

| [Preparation Example 2] | Aqueous injection |
|---|---|
| Human mature chemerin | 200 mg |
| Sodium chloride | 18 mg |
| Water for injection | to 2 mL in total volume |

In accordance with the above ratios among the ingredients, human mature chemerin and sodium chloride are dissolved in water for injection to make an aqueous injection.

| [Preparation Example 3] | Lyophilized-type aqueous injection |
|---|---|
| Human mature chemerin | 100 mg |
| Albumin | 100 mg |
| Sodium chloride | 16 mg |
| Water for injection | to 2 ml in total volume |

In accordance with the above ratios among the ingredients, human mature chemerin, albumin, and sodium chloride are dissolved in water for injection, and then lyophilized to make a lyophilized-type aqueous injection. When used, it is dissolved in 2 mL of water for injection to reconstitute an aqueous injection.

INDUSTRIAL APPLICABILITY

The pharmaceutical composition for treatment of diabetes according to the present invention comprising human mature chemerin augments the hypoglycemic action and glucose uptake promoting action of insulin. Therefore, the present invention can be used, either alone or in combination with insulin, as an agent to treat diabetes, in particular type 2 diabetes characterized by insulin resistance or reduced insulin secretion.

Sequence Listing

We claim:

1. A method for treatment of diabetes in a patient in need thereof comprising administering to the patient a therapeutically effective amount of human mature chemerin.

2. The method according to claim 1, wherein the diabetes is type 1 diabetes or type 2 diabetes.

3. The method according to claim 1, wherein the diabetes is type 2 diabetes.

4. The method according to claim 1, further comprising concurrently administering insulin.

5. The method according to claim 1, comprising administering the human mature chemerin in the form of an injection.

6. The method according to claim 5, wherein the injection is an aqueous preparation comprising the human mature chemerin.

7. The method according to claim 5, wherein the injection comprises a lyophilizate comprising the human mature chemerin.

8. The method according to claim 1, wherein the human mature chemerin comprises the amino acid sequence of SEQ ID NO: 5.

* * * * *